(12) United States Patent
Kammeijer et al.

(10) Patent No.: US 8,026,268 B2
(45) Date of Patent: Sep. 27, 2011

(54) METHOD FOR SCAVENGING RADICALS WITH UROCANIC ACID, DERIVATIVES AND ANALOGUES

(75) Inventors: Arthur Kammeijer, Amsterdam (NL); Joannes Dositheus Bos, Heemstede (NL)

(73) Assignee: Academisch Ziekenhuis bij de Universiteit van Amsterdam, Amsterdam (NL)

( * ) Notice: Subject to any disclaimer, the term of this patent is extended or adjusted under 35 U.S.C. 154(b) by 325 days.

(21) Appl. No.: 11/289,237

(22) Filed: Nov. 29, 2005

(65) Prior Publication Data

US 2006/0106108 A1    May 18, 2006

Related U.S. Application Data

(63) Continuation of application No. 10/019,510, filed as application No. PCT/NL00/004439 on Jun. 23, 2000, now Pat. No. 7,056,938.

(30) Foreign Application Priority Data

Jun. 25, 1999    (EP) .................................... 99202066

(51) Int. Cl.
*A61K 31/415*    (2006.01)
*A61K 31/41*    (2006.01)
(52) U.S. Cl. ............ 514/400; 424/59; 424/60; 424/401; 524/399; 524/365; 524/254; 524/427
(58) Field of Classification Search .................... 424/59, 424/60, 400, 401; 514/399, 400
See application file for complete search history.

(56) References Cited

U.S. PATENT DOCUMENTS

| 3,515,789 | A | * | 6/1970 | Roberts ..................... 514/400 |
| 5,620,680 | A | * | 4/1997 | Stab et al. .................. 424/59 |
| 5,723,482 | A | | 3/1998 | Degwert et al. |
| 6,133,318 | A | | 10/2000 | Hart |
| 6,281,244 | B1 | | 8/2001 | Schneider et al. |

FOREIGN PATENT DOCUMENTS

| JP | 7486524 | 8/1974 |
| JP | 49086524 | 8/1974 |
| JP | 6024978 | 2/1994 |
| JP | 8507752 | 8/1996 |
| JP | 8508474 | 9/1996 |
| WO | WO 94/20065 | 9/1994 |

OTHER PUBLICATIONS

NationMaster—Encyclopedia: Urocanic acid, table, other names.*
Miller et al, The conversion of Urocanic acid to Formamidinoglutaric acid, Journal of Biological Chemistry, 1957, p. 365:381.*
Mohammad et al. abstract, Tetrahedron Letters, vol. 35, issue 28, 1994 p. 4906.*
Kammeyer et al., Biochemica et Biophysica Acta, 1428, 1999 pp. 117-120.*

(Continued)

*Primary Examiner* — Jeffrey S. Lundgren
*Assistant Examiner* — Savitha Rao
(74) *Attorney, Agent, or Firm* — Robert D. Katz; Copper & Dunham

(57) ABSTRACT

The invention relates to antioxidants or radical scavengers and their reaction products. The invention provides compounds and compositions for use in methods for scavenging radicals or for modulating the immune response comprising urocanic acid or salts, derivatives, functional equivalents and analogues thereof.

7 Claims, 5 Drawing Sheets

OTHER PUBLICATIONS

Figure 1:
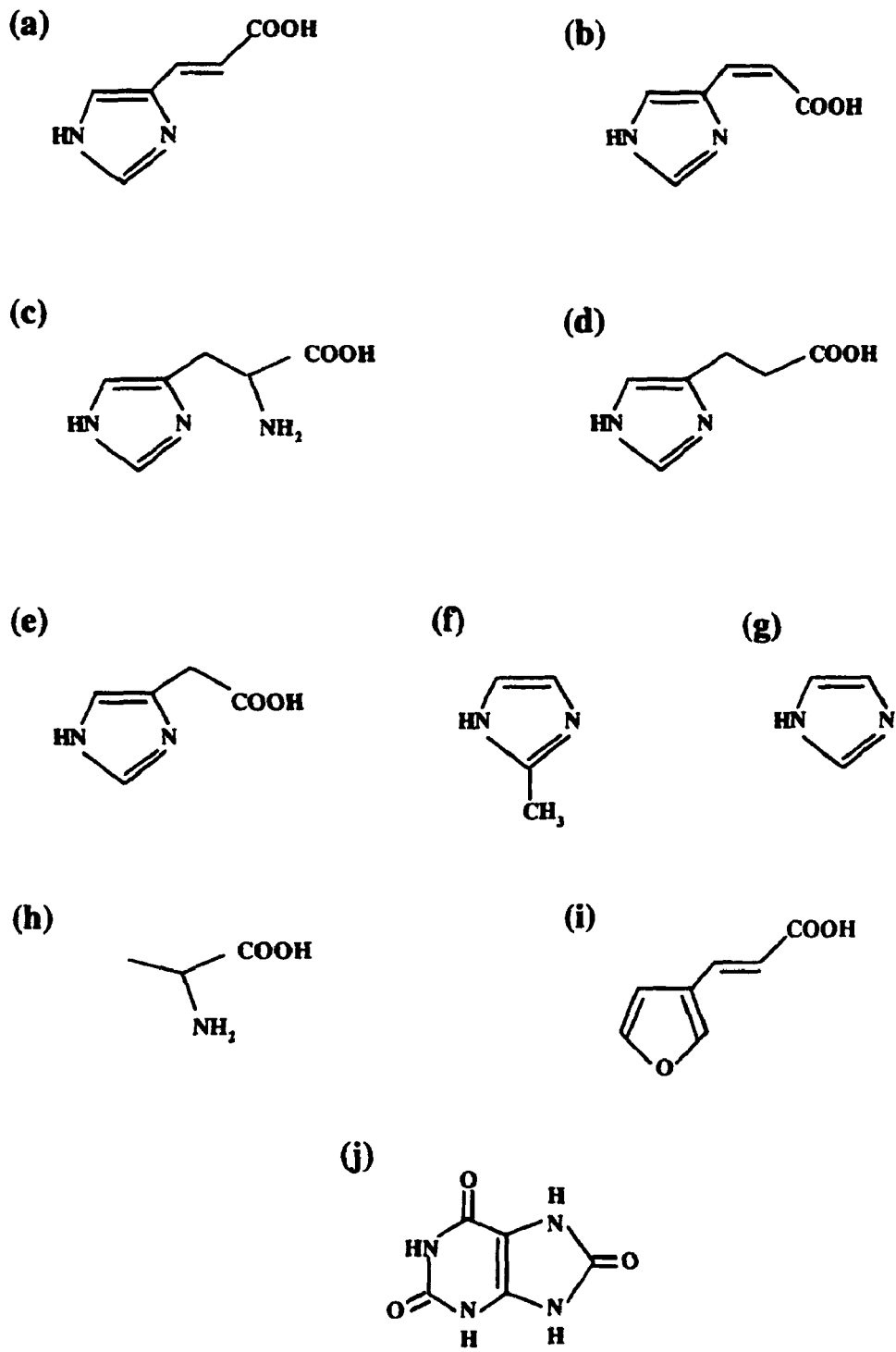

Kammeyer, A. et al., "Oxidative Breakdown and Conversion of Urocanic Acid Isomers by Hydroxyl . . . ," Biochimica et Biophysica Acta, 2001, 277-285, vol. 1526.

Filipec, M. et al., "The Effect of Urocanic Acid on Graft Rejection in an Experimental Model of Orthotopic . . . ," Graefe's Arch. Clin. Exp. Ophthalmol., 1998, 65-68, vol. 236.

Kammeyer, A. et al., "Oxidative Conversion of Trans- and Cis-Urocanic Acid by Hydroxly Radicals . . . ," International Congress on Photobiology, 2000, abstract.

Zhong, Z. et al., "L-Glycine: A Novel Antiinflammatory, Immunomodulatory, and Cytoprotective Agent," Curr. Opin. Clin. Nutrition and Metabolic Care, 2003, abstract.

Staeb, F. et al., "Novel Antioxidants. New Strategies in Product Stabilization and Skin Protection," SOFW J., 1998, Abstract, vol. 124, No. 10.

Marone, G. et al., "Role of Histamine and its Metabolites in the Homeostatic Control of the Immunological . . . ," Folia Allergol. Immunol. Clin., 1981, Abstract, vol. 28, No. 3.

* cited by examiner

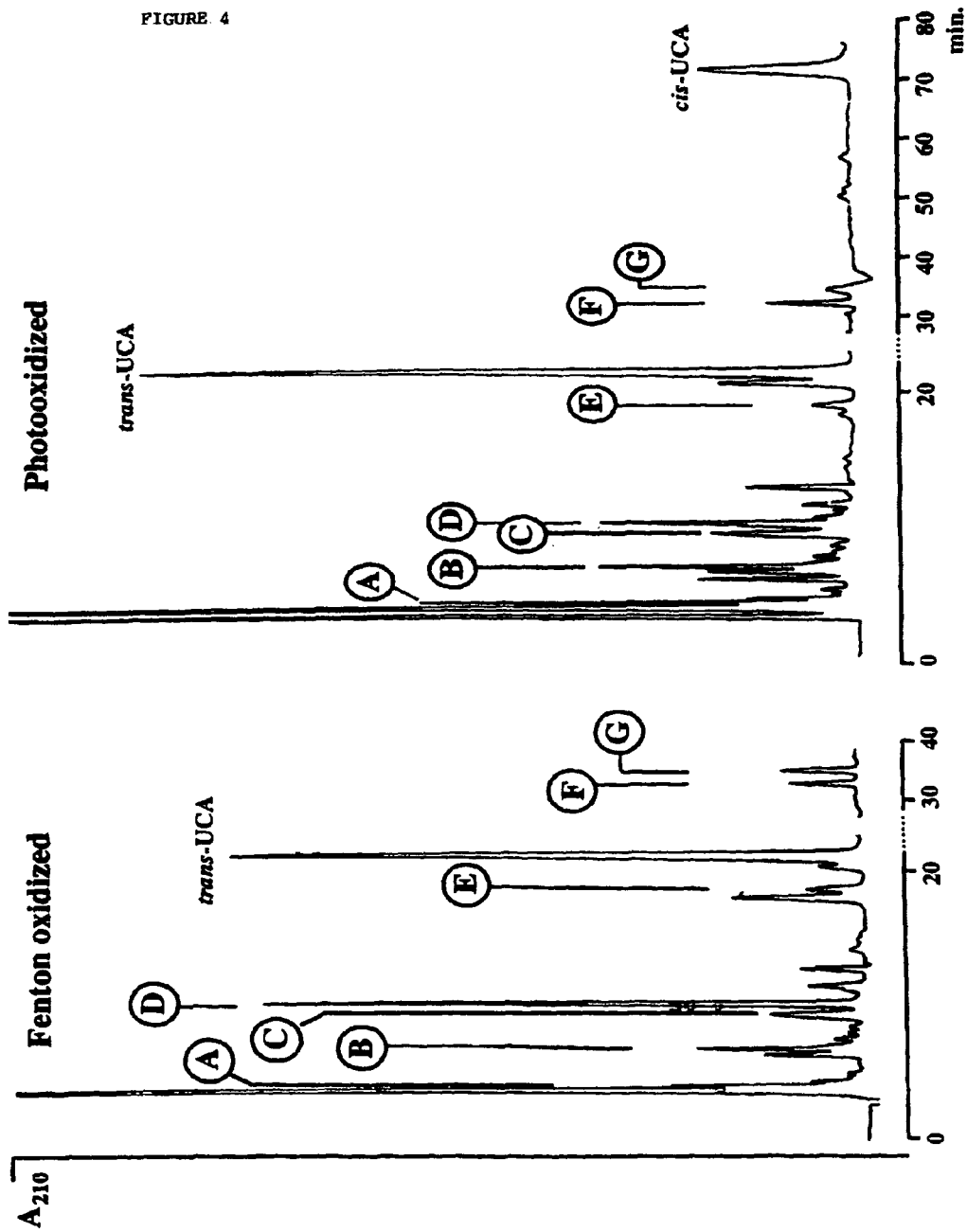

METHOD FOR SCAVENGING RADICALS WITH UROCANIC ACID, DERIVATIVES AND ANALOGUES

This application is a continuation of U.S. patent application Ser. No. 10/019,510 filed on May 9, 2002, now U.S. Pat. No. 7,056,938 which is a 371 of PCT/NL00/004439 filed on Jun. 23, 2000.

The invention relates to antioxidants or radical scavengers and their reaction products.

Trans-urocanic acid (trans-UCA) is a major ultraviolet (UV) absorbing component of the human epidermis. Absorption of UV radiation from the UV-C region (200-290 nm) into the UV-A-I region (340-400 nm) causes photoisomerization of trans-UCA into cis-UCA in vivo as well as in vitro [1-3]. Because of this property, trans-UCA has been used as natural sunscreen agent [4]. This use had later been minimized since it became clear that photoproduct cis-UCA can mimic some of the effects of UV on immunity, suggesting that this compound is an important mediator of UV-induced immunosuppression [5], however, at the moment it is not clear what the main role of UCA or its mode of action is in the context of immunomodulation. Although experiments in vivo supply evidence for the immuno-suppressive potential of cis-UCA (8-12), it is remarkable that in a number of cell cultures (in vitro) suppression was not found (13-17). Similar levels of cis-UCA can be induced by UV-A and UV-B, but nevertheless UV-B is more potent in suppressing contact hypersensitivity than UV-A (18).

The invention provides compounds and compositions for use in methods for scavenging radicals or for modulating the immune response comprising urocanic acid or salts, derivatives, functional equivalents and analogues thereof. Said compounds, compositions and methods as provided by the invention are based on the novel insight that urocanic acid isomers are radical scavengers and serve as natural antioxidants in the body, in particular in skin. UV exposure of the skin causes an increased level of oxidative stress with the inherent formation of reactive (hydroxyl) radicals. It is shown herein that (salts of) urocanic acid isomers or functional equivalents such as imidazole equivalents and imidazolone derivatives thereof, in particular physiologically (in the body) occurring imidazole compounds for example act as physiological antioxidants capable of efficiently protecting lipid phases of biological membranes and proteinaceous substances in aqueous environments against the action of radicals such as hydroxyl, singlet oxygen or other reactive odd-electron species. These species can be generated from hydrogen peroxide upon UV irradiation, and from hydrogen peroxide in presence of metal ions (e.g. $Fe^{2+}$), the Fenton reaction. Both types of reaction can occur in the epidermis [6]. Under conditions of oxidative stress, enhanced by exposure to UV [7], it is evident that UCA isomers will encounter the randomly produced hydroxyl radicals in situ.

The invention thus provides in one embodiment a method for scavenging radicals in a substance comprising providing said substance with urocanic acid or a functional equivalent thereof, such as a salt or functionally related imidazole compound. Preferably, trans-urocanic acid or a functional equivalent thereof is used, being most active or being least immunosuppressive. Using urocanic acid or equivalents thereof as antioxidant or radical scavenger is advantageous over using other antioxidants, such as vitamin E, which are commonly not or only partly soluble in water, whereas urocanic acid or its analogues dissolve easily in aqueous solutions. Especially where said substance comprises a food product or cosmetic product, which are commonly water based, using urocanic acid or its functional equivalent as provided by the invention is advantageous over water insoluble antioxidants. Both isomers are water soluble hydroxyl radical scavengers and can be used in the water phase of numerous emulsions. Furthermore, urocanic acid isomers, being natural components of the body, are essentially non-toxic, which additionally is advantageous when preparing a food product or cosmetic product.

In another or subsequent embodiment, the invention thus provides a method for scavenging radicals in a tissue, for example subjective to oxidative stress, comprising providing said tissue with urocanic acid, e.g. the invention provides use of urocanic acid or equivalents thereof for the preparation of a pharmaceutical or cosmetic composition, for example for the treatment of oxidative stress, such as for example manifested in wrinkles and other signs of ageing tissue, in particular skin. Oxidative stress in living organisms and their tissues, in particular the oxidation of proteins, has been implicated in the phenomenon of ageing, wrinkling, acute damage of proteins, ischemia reperfusion, atherosclerosis, and many chronic diseases, such as psoriasis, scleroderma, lupus erythematosus, allergic contact dermatitis, vitiligo, lichen planus and graft-versus-host disease, or which treatment the invention now provides a pharmaceutical or cosmetic composition comprising urocanic acid or functional equivalent thereof. Such a composition is advantageously also used for immuno modulatory purposes.

In yet another embodiment, the invention provides use of an oxidation product of urocanic acid or equivalents thereof (such as salts or related imidazole compounds having similar effect) for the preparation of a pharmaceutical composition, in particular wherein said product is an photo-oxidation product. Herein is used the novel insight that as a consequence of radical scavenging, epidermal UCA isomers are converted by reactive oxygen species (ROS) into oxidation products with biological i.e. immunomodulating effects. In contrast to the photoisomerization of UCA, not much attention has as yet been given to the oxidation of UCA. In particular not to the reaction of UCA isomers with the very reactive hydroxyl radicals. Hydroxyl radicals can be generated from hydrogen peroxide upon UV irradiation, and from hydrogen peroxide in contact with reduced metal ions, e.g. ferrous ($Fe^{2+}$) ions. Both types of reaction can occur in the epidermis (6).

Under conditions of oxidative stress, enhanced by exposure to UV (7), it is evident that UCA isomers will encounter the randomly produced hydroxyl radicals. We now provide the insight that it is in general not cis-urocanic acid per se that provides modulation or repression of immune responses, but oxidation products of urocanic acid, that for example have arisen after ultraviolet light (UV) exposure of for example skin. Herein, urocanic acid scavenges radicals created by UV exposure, is thereby oxidised to for example imidazole containing urocanic acid derivatives, such as imidazole-4-carboxyaldehyde, imidazole-4-acetic acid or imidazole-4-carboxylic acid, which subsequently modulate, suppress or mitigate a mounting immune response of the body to the UV induced tissue damage.

By providing insight into this natural mechanism, we provide insight in immune modulating mechanisms that are at work to keep (overly strong) immune responses, for example directed at UV exposure at bay. The invention thus provides use of a pharmaceutical composition comprising an oxidation product of urocanic acid for modulating immune responses against various stimuli, thereby mimicking a, previously unknown, natural action of said product. Herewith the invention provides a method to modulate an immune response of an animal, for example a human being, comprising treating said animal with a pharmaceutical composition comprising an oxidation product of urocanic acid, for example wherein said product is an imidazole such as imidazole-4-carboxyaldehyde, imidazole-4-acetic acid or imidazole-4-carboxylic acid or an imidazolon derivative of urocanic acid such as 3-(4-imidazolon-2-yl)-acrylic acid and 3-(4-imidazolon-5-yl)-acrylic acid. In particular the invention provides the use of one or more UCA photo-oxidation products as immuno modulator in various skin diseases, such as psoriasis or dermatitis. Furthermore, the invention provides a pharmaceutical composition comprising urocanic acid or functional equivalent thereof for its radical scavenging properties, whereby said composition is additionally used as immuno modulator, optionally already comprising oxidation products having immune modulatory function.

The invention is further explained in the detailed description without limiting the invention thereto.

DETAILED DESCRIPTION

Trans-UCA, cis-UCA, related imidazoles and non-imidazole compounds were tested with regard to their ability to compete with deoxyribose to scavenge hydroxyl radicals. On exposure to hydroxyl radicals deoxyribose is degraded into malondialdehyde, which reacts with thiobarbituric acid to form a pink chromogen. Powerful hydroxyl-radical scavengers will compete with deoxyribose, resulting in a reduced amount of malondialdehyde [22]. Ten compounds, UCA, UCA analogues, alanine and uric acid (FIG. 1) were tested on their ability to scavenge hydroxyl radicals.

Figure 2:
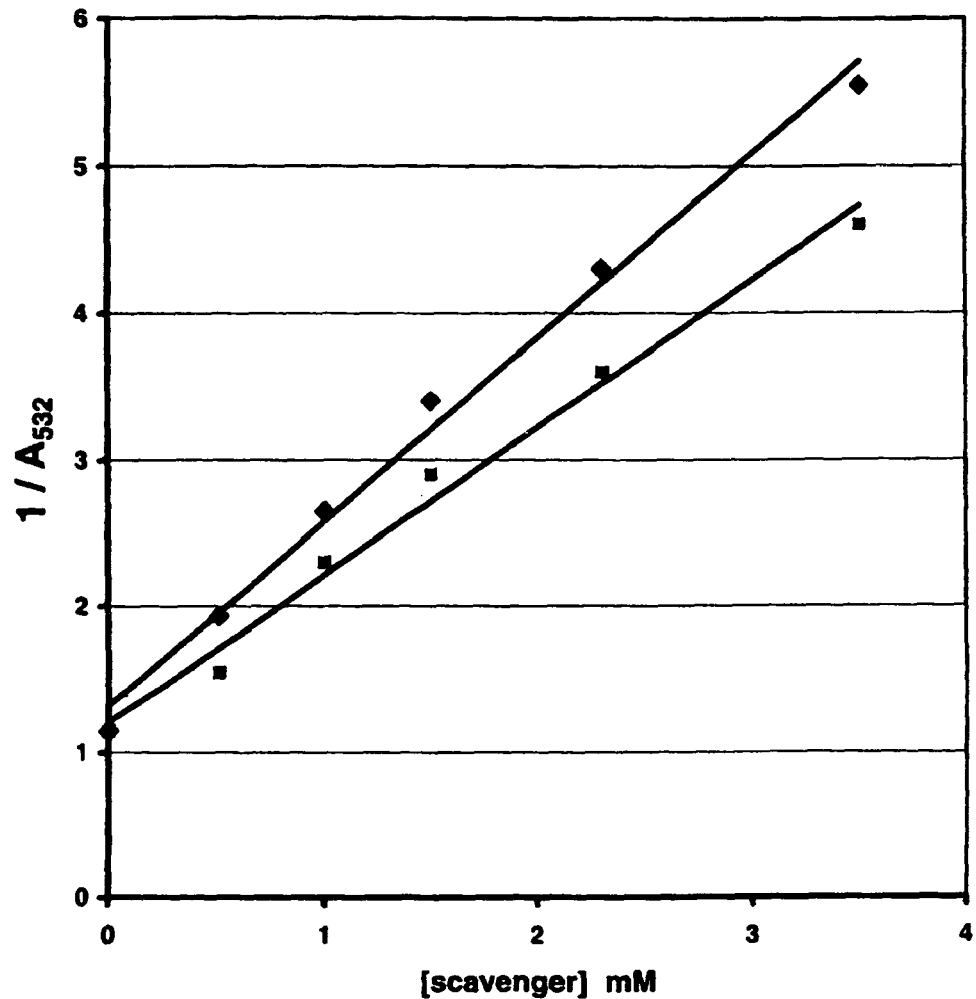

Method: the deoxyribose (dR) degradation test. The test was analogous to an earlier described method [22]. Briefly, the reactions were performed in 5 mL screw cap glass tubes in a final volume of 1.0 mL sodium phosphate buffer (50 mM; pH 7.2), containing 3.0 mM 2 deoxy-D-ribose, 0.5 mM hydrogen peroxide and one of the test compounds at graded concentrations. The reaction was started by the addition of premixed disodium EDTA and ferrous iron solution (final concentrations 0.5 mM and 0.2 mM, respectively). The mixture was left for 15 minutes at room temperature. After addition of 1.0 mL 1% thiobarbituric acid in 50 mM NaOH and 0.75 mL 2.8% trichloroacetic acid, the tubes were heated for 20 minutes in a boiling water bath. The pink color was read at 532 nm and reciprocal absorption values were plotted against the concentration of the test compound after subtraction of appropriate blanks. A series of six duplicate determinations from test compound dilutions was employed to construct a graph slope for the calculation of a rate constant value. The mean, SD, number of rate constants and the percentage of inhibition of deoxyribose degradation, calculated for each test compound, are listed. Results. All second-order rate constants for reaction with hydroxyl radicals and, in addition, the percentage inhibition of deoxyribose degradation with equimolar concentrations (3 mM) of scavenger are summarized in Table 1. A typical graph with slopes to derive rate constants from is shown in FIG. 2 for both UCA isomers. Trans-UCA and cis-UCA are substantially more powerful in scavenging hydroxyl radicals (8.0 and $7.1 \times 10^9$ $M^{-1} \cdot s^{-1}$, respectively), than the other 4-(5-)-substituted imidazoles, including L-histidine ($2.6 \times 10^9$ $M^{-1} \cdot s^{-1}$). L-histidine, the precursor of UCA, was included as a known moderate scavenger [22-24] with structural similarities to UCA. L-alanine was used as a known poor scavenger [22]. Trans-FAA was tested as a non-imidazole acrylic acid derivative, having a furan ring instead. This substitution yielded a very poor scavenging ability.

Other 4-(5-) substituted imidazole analogues, dihydrourocanic acid or 3-(imidazol-4-yl)-propionic acid and imidazole-4-acetic acid, showed moderate scavenging ability, comparable to histidine. Unsubstituted imidazole and its 2-methyl derivative appeared to be stronger scavengers than the UCA isomers. The well-known hydroxyl radical scavenger uric acid showed an excellent abilitiy ($27.8 \times 10^9$ $M^{-1} \cdot s^{-1}$).

Trans-UCA and cis-UCA, two epidermal compounds, are good hydroxyl radical scavengers; their ability is less than that of uric acid, but larger than that of the other 4-(5-) substituted imidazoles, e.g. histidine.

Trans-UCA and cis-UCA are herein recognized as good hydroxyl radical scavengers. Both isomers occur in substantial concentrations in the epidermis, the latter in the UV-exposed skin. There is strong evidence for the occurrence of hydroxyl radicals in the epidermis, especially upon UV irradiation [7]. Normal human skin contains approximately 200 µM iron [26,27], predominantly complexed to ferritin. The release of free ferrous ions by UV irradiation [28] and the presence of hydrogen peroxide [29,30] are prerequisites for the generation of hydroxyl radicals. Other reports indicate the UV-induced presence of hydroxyl radicals indirectly since their effects on epidermal constituents could be neutralized with antioxidants [31, 32].

UCA is an imidazole compound and several other imidazole derivatives have already been shown to be good hydroxyl radical scavengers, e.g. histidine [22-24], histamine [33], histidine containing dipeptides [24,34], cimetidine and other histamine ($H_2$) receptor antagonists [35]. This study reveals that several other imidazoles show similar properties (Table 1). Hydroxyl radicals can react with the imidazole ring to form imidazolone derivatives. Their formation has led to the proposal to use the imidazolones of histidine and histamine as markers for oxidative stress [23,33]. The importance of the imidazole ring in UCA molecules was also demonstrated in our experiments. The poor scavenging ability of trans-FAA, having a furan ring instead, was a remarkable contrast. Furthermore, the presence of the acrylic acid moiety in UCA molecules conjugated with the imidazole ring may account for its increased scavenging ability towards hydroxyl radicals as compared to the other 4-(5-) substituted imidazoles. Unsubstituted imidazole and its 2-methyl derivative are stronger hydroxyl radical scavengers, accentuating that the presence of an imidazole ring is a prerequisite for sufficient hydroxyl radical scavenging ability. However, these compounds do not occur physiologically and are harmful ($LD_{50}$ oral rat 220 mg/kg for imidazole and 1500 mg/kg for 2-methylimidazole).

Trans-UCA and cis-UCA do occur physiologically, mainly in the epidermis, with relatively high concentrations. Our findings point to a new physiological role for the UCA isomers, besides the suggested roles of trans-UCA as natural sunscreen agent and cis-UCA as immunosuppressant. Trans-UCA and cis-UCA may be major epidermal hydroxyl radical scavengers, providing a new view on the antioxidant status of the skin. The findings that 1. UCA isomers are good hydroxyl radical scavengers, though not as strong as uric acid, and that 2. the UCA isomers already occupy relatively high concentrations in the skin, create possibilities to apply the UCA isomers as non-toxic antioxidant additives in food and cosmetics in relatively high concentrations. Trans-UCA (commercially available) should be preferred, because cis-UCA may exert immunosuppressive effects.

In contrast to the photoisomerization of UCA, not much attention has as yet been given to the oxidation of UCA. In particular, the reaction of UCA isomers with the very reactive hydroxyl radicals should be explored. Hydroxyl radicals can be generated from hydrogen peroxide upon UV irradiation, and from hydrogen peroxide in contact with reduced metal ions, e.g. ferrous ($Fe^{2+}$) ions. UV-A irradiation of trans-UCA or cis-UCA with hydrogen peroxide only results in UCA photoisomerization and not in UCA photooxidation. The lack of correlation between UV-A-induced cis-UCA formation and immunosuppression (18) may be another indication for a role of UCA-oxidation products in skin immunology. These compounds can either be formed in the presence of hydrogen peroxide upon UV-B irradiation or by a Fenton reaction; both reaction types leading to comparable sets of oxidation products as determined by chromatographic patterns. The common oxidizing species of both reaction types is most likely the hydroxyl radical. Starting the oxidation with trans-UCA or with cis-UCA yielded similar chromatographic patterns. In relation with hydroxyl radical scavenging of the UCA isomers, it should be noted that UCA isomers may as well interfere with UV-induced immunosuppression through scavenging of radical species. The presence of the acrylic acid moiety in UCA molecules conjugated with the imidazole ring may account for its increased scavenging ability towards hydroxyl radicals as compared to non-conjugated imidazoles, such as histidine and histamine. It may also account for the diversity of the formed oxidation products.

Materials and Methods

High Performance Liquid Chromatography (HPLC)

Trans-UCA and cis-UCA were separated from each other and from several UCA oxidation products on a 4.6×250 mm Alltima $C_{18}$ and a Luna $C_{18}$ reversed-phase column (Alltech, Deerfield, Il and Phenomenex, Torrence, Calif., resp.) with a flow of 0.8 mL/min, delivered by P-3500 HPLC-pumps (Pharmacia, Uppsala, Sweden). Samples of 20 to 200 μL were injected by a Promis II autosampler (Spark Holland, Emmen, The Netherlands) and chromatographic data were recorded on an SP 4270 integrator (Spectra Physics, San Jose, Calif.). Peak area data from samples were only processed under identical HPLC circumstances. A UV-detector (Applied Biosystems, model 759A, Foster City, Calif.) was set for 226 nm detection. Isocratic elution was performed with 10 mM ammonium formate buffer, containing 0.2-0.8 mM tetrabutylammonium(TBA) formate and 1% acetonitrile (pH 7.2). Collected fractions were acidified with formic acid up to a final concentration of 100 mM and passed through $C_{18}$ solid phase extraction columns (JT Baker, Deventer, The Netherlands) in order to remove TBA.

Photooxidation

A 1-cm quartz cuvette, filled with 1.4 mL sample, was placed in the parallel beam of a filtered 1000 W xenon arc lamp (Oriel, Stratford, Conn.). The samples were magnetically stirred during irradiation. To minimize infrared (heat) and visible radiation, the beam was passed through a water filter (7 cm), reflected by a dichroic mirror and filtered through a 1-mm UG11 filter. Short-wave cut off was achieved by passing the beam through WG280, WG305 or WG335 filters with 3 mm thickness each (Schott-Jena, Mainz, Germany). Xenon lamp emission filtered through WG280 included UV-C, UV-B and UV-A; through WG305 UV-B and UV-A and through WG335 only UV-A was included. Two narrow bands in the UV-B and UV-A spectral regions were selected to monitor the xenon-arc emission. The probe of a calibrated EG&G 550 radiometer (Salem, Mass., USA) was equipped with a neutral density filter and narrow band filter type UV-M-IL (Schott-Jena) with a transmission maximum of 21% at 303 nm and a half-width of 11.5 nm to monitor UV-B or with a type UV-PIL (Schott-Jena) with a transmission maximum of 46% at 363 nm and a half-width of 7.7 nm to monitor UV-A. Transmission spectra of the optical filters were checked on a Perkin Elmer Lambda 40 UV/VIS spectrometer (Norwalk, Conn., USA).

Additional irradiations were performed with fluorescent tubes TL12, used as a UV-B source, and TL10R, used as a UV-A source (Philips, Eindhoven, The Netherlands), on samples that were magnetically stirred in small Petri dishes. The UV-B output was measured with an IL 443 phototherapy radiometer, fitted with a SEE 1240 silicon detector probe and the UV-A output with an IL 442A phototherapy radiometer with a SEE 115 detector probe (International Light, Newburyport, Mass., USA).

Fenton Oxidation.

UCA isomers (10 or 40 μM) were oxidized with a hydroxyl-radical-generating system that consisted of various concentrations of ferrous ions (10-500 μM) and a fixed hydrogen peroxide concentration of 500 μM (the Fenton reagent), either in a sodium phosphate (10 or 20 mM) medium of pH 7.2, or in ultrapure water. In addition, two hydroxyl-radical-generating systems with copper ions ($Cu^{2+}$) were used, consisting of 50 μM $Cu^{2+}$ with either 500 μM hydrogen peroxide or 5 mM ascorbic acid.

Synthesis of reference compound
imidazole-4-carboxaldehyde (4-formylimidazole)

4-(Hydroxymethyl)imidazole-HCl (4 mmol) was stirred together with sodium bicarbonate (6 mmol) in 4 ml methanol for 1 hour at room temperature. The methanol was evaporated and the residue was extracted with a chloroform/methanol 1:1. After centrifugation at 3500 rpm for 5 minutes the supernatant was evaporated and the residue was taken up in 20 ml hot dioxane. 4.4 g manganese dioxide (activated; for synthesis) was added, followed by a reflux reaction for 2 hours. Manganese dioxide was removed by filtration and the filtrate was evaporated. Crystallization was carried out in methanol. The yield was 95 mg of fine off-white crystals, 25% of maximum yield. The melting range was 168-169° C.:173-175° C.). Melting range of starting material was 108-111° C. and of the oxidation product imidazole-4-carboxylic acid 294-295° C. UV (water) $\lambda_{max}$ (log ϵ) 257 nm (3.85).

Results

UCA Isomers and Photooxidation

Figure 3A:
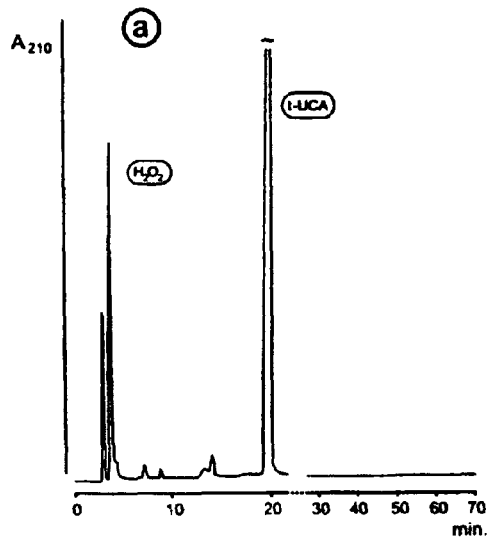
Figure 3B:
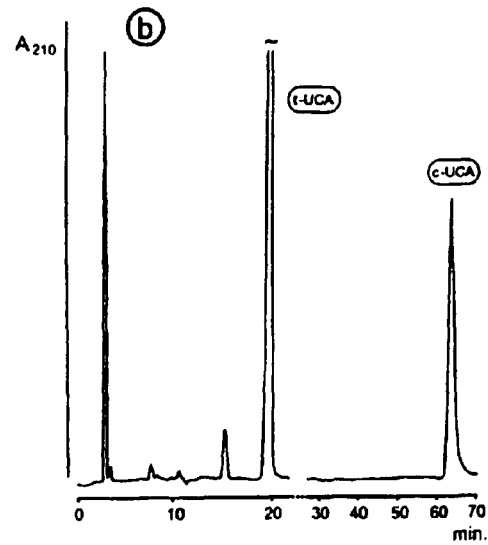
Figure 3C:
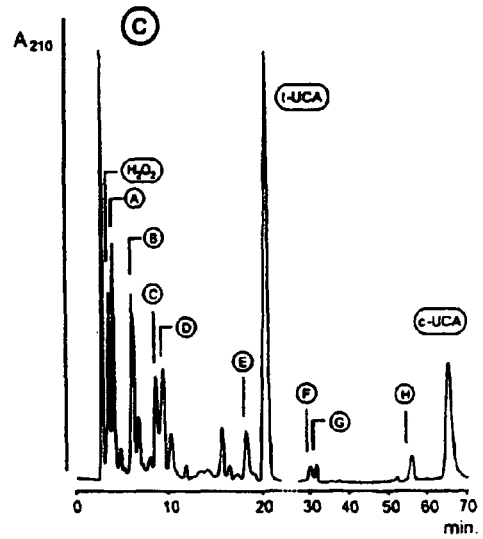

The O—O bond of hydrogen peroxide can be cleaved by UV radiation to yield hydroxyl radicals. Because both UCA isomers could effectively scavenge hydroxyl radicals, it is to be expected that UCA will be degraded and/or converted into oxidation products. The ability of simulated solar UV radiation to convert trans-UCA in the presence of hydrogen peroxide into photooxidation products was tested in vitro and analyzed by reversed-phase HPLC analysis. Hydrogen peroxide eluted close to void volume and trans-UCA and cis-UCA eluted with markedly different elution times of 20 and 64 min (FIG. 3a-d). The unirradiated control sample did not show any interaction between trans-UCA and hydrogen peroxide (FIG. 3a). Exposing 80 μM trans-UCA in the absence of hydrogen peroxide at pH 7.2 to WG280-filtered xenon-arc emission (including UV-C and UV-B) resulted only in the formation of cis-UCA via the process of photoisomerization (FIG. 3b). However, when trans-UCA was irradiated in the presence of 500 μM hydrogen peroxide under identical conditions, many additional peaks appeared in the chromatograms and both trans-UCA and cis-UCA peaks were strongly reduced (FIG. 3c), indicating a certain photochemical conversion or breakdown. Eight main photooxidation products were recognized as new peaks based on retention times and were assigned in the chromatogram (FIG. 3c).

Figure 3D:
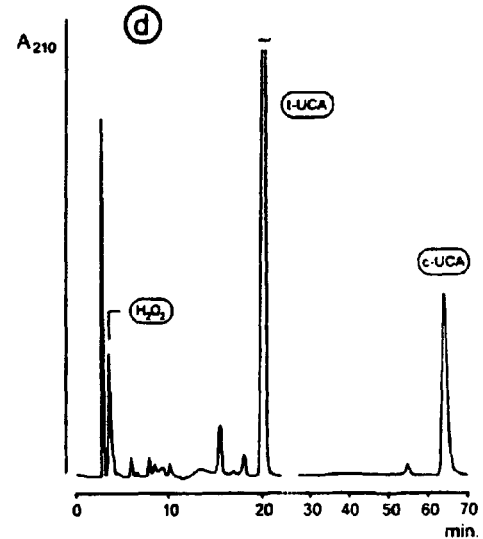

In contrast, when exposures were performed with simulated solar radiation from which both UV-C and UV-B were blocked out by a WG335 filter, virtually no photo-oxidation products were found (FIG. 3d). Only UCA photoisomerization was apparent, which is in accordance with earlier reports (2, 3). The ratio of trans-UCA to cis-UCA photoisomerization was not affected by the degree of photooxidative breakdown. Blocking out UV-C by the use of the WG305 filter showed intermediate results (Table 2). This irradiation condition has the closest simulation with the spectral UV distribution of terrestrial solar radiation produced by an overhead sun on a bright day. Tests with the fluorescent lamps TL 12 (UV-B and UV-A; some UV-C) and TL10R (UV-A) confirmed the above findings that UV-B and UV-C have photooxidative ability. Although the UV-A dose of the fluorescent lamp was much higher than that of UV-B, the yield of UCA photo-oxidation products was much lower with UV-A (Table 2). The formation of photo-oxidation products was quantified by summing the eight major peak areas (in arbitrary units; peaks A-H). The degree of photo-oxidative breakdown, the yield of photo-oxidation products and the degree of UCA photoisomerization under different irradiation conditions were summarized in Table 2. Taking the various emissions of these UV sources into account, the photo-oxidative ability of UV radiation became substantial with wavelengths shorter than approximately 320 nm. Experiments with cis-UCA yielded similar results, except that cis-UCA/trans-UCA ratios were increased in this series (data not shown).

UCA Isomers and Fenton Oxidation

In the next series of experiments we studied the Fenton oxidation of UCA, representing another natural oxidation process. Trans-UCA and cis-UCA isomers were Fenton oxidized by ferrous ions ($Fe^{2+}$) and hydrogen peroxide at physiological concentrations. The initial hydrogen peroxide concentration was 500 µM and the ferrous ion concentration was varied from 0 to 500 µM. In all Fenton-oxidation reactions the degree of UCA-isomer breakdown was calculated from their reduced peak areas. The oxidation reaction must have been completed within 2 minutes for all reaction conditions, because no further breakdown was observed after prolonged incubation. Hydrogen peroxide without $Fe^{2+}$ had no effect on the UCA isomers at all; however, $Fe^{2+}$ without hydrogen peroxide resulted in a slow breakdown of UCA isomers after prolonged incubation (data not shown).

The sequence order of addition of the two Fenton reagents did not markedly affect the UCA breakdown and yield of oxidation products, except at a low UCA concentration of 10 µM. When $Fe^{2+}$ was added after hydrogen peroxide, a larger breakdown and a smaller yield of Fenton-oxidation products were observed, whereas the reversed-sequence order gave opposite results (data not shown).

When the Fenton reaction was performed in water instead of phosphate buffer, the oxidative breakdown of trans-UCA was enhanced irrespective of the UCA concentration. The turbidity seen in reactions performed in phoshate buffer (10 mM) with high $Fe^{2+}$ concentration (>100 µM) was probably due to the formation of insoluble iron phosphate, thereby reducing the free availability of $Fe^{2+}$. Table 3 summarizes the difference between water and phosphate medium for trans-UCA at an initial concentration of 40 µM with respect to its breakdown and the formation of Fenton-oxidation products. Similarly to the photo-oxidation experiments, the peak areas of the 8 major oxidation products were summed. Comparable results were obtained with cis-UCA (data not shown), which finding is in accordance with the comparable rate constants of trans-UCA and cis-UCA in the deoxyribose degradation experiment (Table 1). A close resemblance was observed between the chromatographic patterns of UCA Fenton oxidation products (not shown) and those of UCA photo-oxidation products. Three of them has been identified (vide infra).

When two other hydroxyl-radical-generating systems based on copper ions ($Cu^{2+}$) were investigated with trans-UCA, the combination of $Cu^{2+}$ (50 µM) and ascorbic acid (5 mM) without hydrogen peroxide caused an almost complete breakdown of trans-UCA (3% left), whereas the system with $Cu^{2+}$ (50 µM) and hydrogen peroxide (500 µM) showed little effect (88% trans-UCA left). Evaluation of the data was difficult with the ascorbate system, because several interfering peaks had occurred in the chromatograms, which were probably derived from ascorbic acid and its oxidation products. Both systems are considered to be of minor importance for the situation in vivo, but these results indicate similarities in oxidative behaviour of the UCA isomers, independent of the nature of the hydroxyl-radical-generating system.

UCA Isomers and Fenton Oxidation.

In another series of experiments we studied the Fenton oxidation of UCA, representing another natural oxidation process. The initial hydrogen peroxide concentration was 500 µM in all experiments and the ferrous ion concentration was varied from 0 to 400 µM. Four sets of conditions were compared: 1. $Fe^{2+}$ in phosphate buffer pH 7.2, 2. $Fe^{2+}$ in phosphate buffer plus EDTA, 3. $Fe^{2+}$ without buffer with a initial pH of 5.5-5.3 and 4. $Cu^{2+}$ in phosphate buffer plus ascorbate. The degree of breakdown was similar for both UCA isomers. Table 3 shows oxidative breakdown of trans-UCA with hydrogen peroxide in increasing order: condition 1<2<4<3.

The addition of $Fe^{2+}$ at final concentrations of 100-400 µM in phosphate buffer caused a turbid solution of insoluble iron phosphate. Under this condition the smallest degree of breakdown was established. A limited availability of free $Fe^{2+}$ is assumed to reduce the oxidative breakdown of UCA. At the other hand, complexation of $Fe^{2+}$ to EDTA did not cause a turbid reaction mixture and a larger breakdown was established (Table 3). The largest breakdown was seen in the absence of phosphate buffer, with a less defined pH value of 5.5 to 5.3, dependent on the UCA concentration (40, 100 or 250 µM). At the start of the Fenton reaction in the unbuffered medium, there was a rapid fall of the pH value from 5.1 to 3.4, with initial concentrations of trans-UCA, hydrogen peroxide and ferrous ions of 250, 500 and 400 µM, respectively. We attribute this effect to the unbuffered liberation of relatively strong acids, such as glyoxylic acid (GLX). Similar results of breakdown, though slightly less pronounced, were obtained with cis-UCA. This finding is in accordance with the comparable second order rate constants of trans-UCA and cis-UCA for hydroxyl radical scavenging (8). Hydrogen peroxide without $Fe^{2+}$ had no effect on the UCA isomers at all; however, $Fe^{2+}$ without hydrogen peroxide resulted in a partial breakdown of the UCA isomers upon prolonged incubation of one day (data not shown).

The primary oxidation products formed are ImCHO and GLX. Additional experiments in which ImCHO was used as starting material, a yield of virtually 100% ImCOOH was obtained after Fenton- or photooxidation. In UCA samples that were highly oxidized (containing <4% UCA) ImCOOH was the major 226 nm absorbing compound, while ImCHO concentration was largely reduced. An additional experiment demonstrated that under this oxidative condition the aldehyde (ImCHO) was oxidized to the carboxylic acid (ImCOOH). GLX was analyzed in lower amounts than ImCHO in all cases studied (Table 3), except for the Fenton oxidation of 40 µM UCA. Trans-UCA and cis-UCA in relatively high concentration of 250 µM were broken down for 78% and 75%, respectively, by the unbuffered. Fenton oxidation system. The yield of oxidation products was proportional with the initial UCA concentration. Remarkably, the yield of ImCHO from cis-UCA was substantially larger than from trans-UCA. In the phosphate buffered Fenton system a comparable breakdown and a comparable yield of oxidation products was recorded, irrespective of the initial UCA concentration range from 40 to 250 µM. In the presence of EDTA, a larger breakdown and a higher yield of oxidation products (in particular ImCHO) resulted (Table 4, section 2). This yield was raised as higher initial UCA concentrations were used. In the unbuffered system, the highest degree of breakdown of all tested systems was recorded. The oxidation product yield was the largest of all systems when the initial UCA concentration was high (250 µM).

When another hydroxyl-radical-generating system, based on copper ions ($Cu^{2+}$) was investigated, the combination of $Cu^{2+}$/ascorbic acid/hydrogen peroxide caused a large breakdown of trans-UCA (Table 3) and a moderate yield of UCA oxidation products, in favor of ImCOOH. Without ascorbic acid, the system with $Cu^{2+}$ (50 µM) and hydrogen peroxide (500 µM) showed little breakdown (88% trans-UCA left; data not shown). For the situation in vivo, one must remember that the epidermal copper content is lower than iron (29).

2.3.4. UCA Compared in Fenton—and Photooxidation

Figure 5:
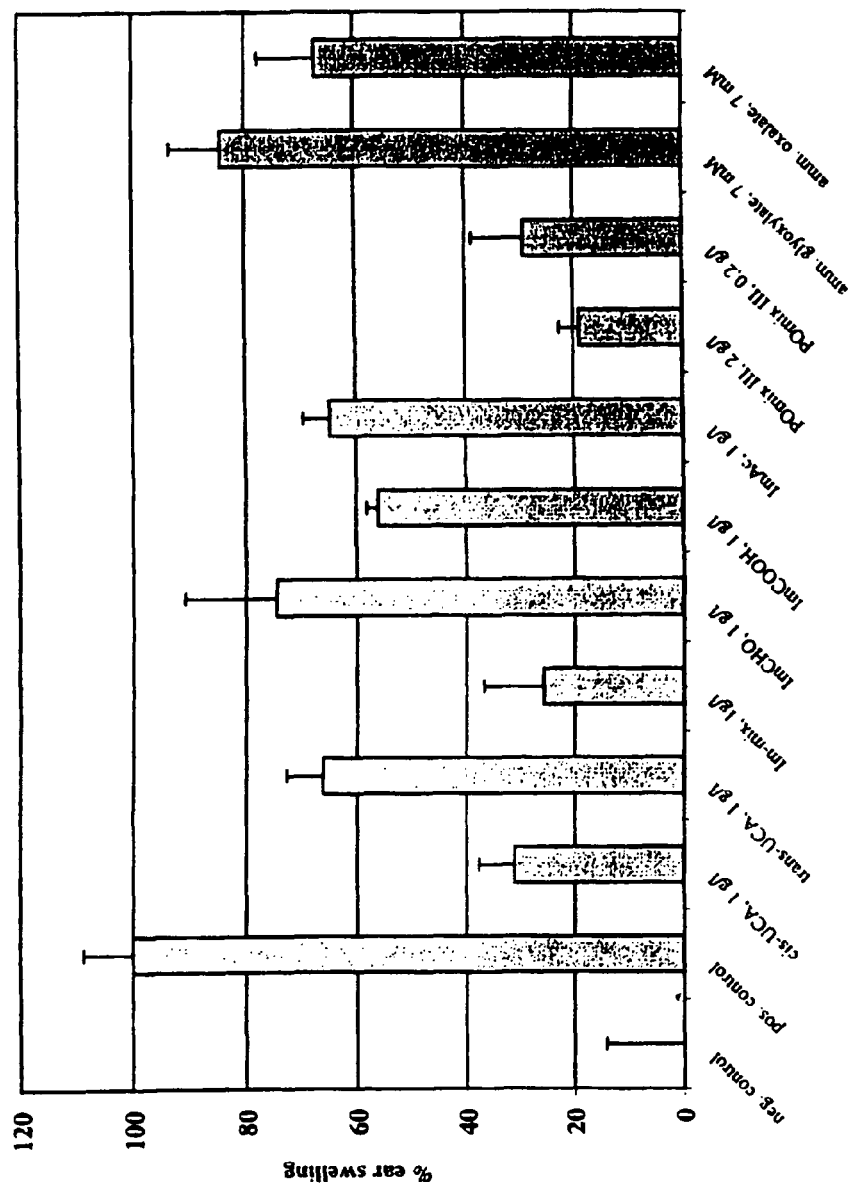

A close resemblance was observed between the chromatographic patterns of UCA Fenton oxidation products and those of UCA photooxidation products (FIG. 5). Also under photooxidation an oxidation inhibiting effect was seen in phosphate of pH 7.2, whereas the yield of oxidation products was in favor of ImCHO In photo-oxidation, the breakdown of cis-UCA was substantially decreased in comparison with the trans isomer. In Fenton oxidation, this effect was less pronounced. The data were given for air saturated solutions. Argon-purging of the solutions, prior to Fenton- or photooxidation, enhanced UCA breakdown as well as the yield of oxidation products, both by a factor 2 to 3. Heating (to 37° C.) of argon-purged solutions slightly enhanced the yield of ImCHO.

The data indicate a discrepancy ('gap') between micromoles of UCA isomer broken down and micromoles of oxidation products formed. The smallest 'gap', though still 52%, was found after the oxidation of cis-UCA in the unbuffered system. Thin layer chromatography (TLC) gave more insight in the 'gap' products, that were not seen in reversed phase chromatography, using UV detection or fluorescence detection. TLC carried out on silica with the eluent isopropanol/ammonia 25% (4:1) showed an array of elutable, partly overlapping fluorescent spots and a fluorescent spot at the start position (data not shown). However, the initial weight of trans-UCA, introduced in a photooxidation experiment with extensive UCA breakdown (<4% of each UCA isomer left over), was not lowered much (~14%) after severe photooxidation. This finding indicated a predominant formation of non-volatile, solid material in stead of gaseous compounds, such as $CO_2$ and water. The TLC pattern and the weighing experiment points to a possible hydroxyl radical initiated chain reaction of UCA, resulting in the formation of substances that may fill the above mentioned gap. These substances may not be fully detected under the chromatographic conditions used for the simultaneous determination of the UCA isomers, ImCHO and ImCOOH.

2.3.5. Inhibition of Contact Hypersensitivity.

The inhibitory effects of the UCA oxidation products are illustrated in FIG. 5. Maximum ear swelling response was normalized to 100%. The largest reduction was obtained with the residue of severely photooxidized UCA (PO mix III), containing less than 4% residual cis-UCA. It resulted in only 19% ear swelling (81% reduction of swelling). Even a tenfold dilution of that mix (0.2 g/l) reduced the ear swelling markedly (29% ear swelling), which is of similar level as the effect of cis-UCA in a concentration of 1 g/l (31% ear swelling). Another remarkable effect was obtained by mixing the three identified imidazoles. When we tested one of the imidazoles alone (1 g/l), only a moderate effect was seen, however, when tested mixed together (1 g/l, each imidazole 0.33 g/l), a synergistic effect was observed (26% ear swelling). Glyoxylic acid and oxalic acid, as ammonium salts, did not exhibit significant inhibition of CHS.

UCA Photo-Oxidation on a Preparative Scale

Concentrations of trans-UCA and hydrogen peroxide were largely increased, as was the UV exposure, to obtain larger amounts of UCA photo-oxidation products as collected fractions from the reversed phase column for further analysis. A typical chromatogram is shown in FIG. 4. Four fractions, designated as $R_t$ 8, $R_t$ 10, $R_t$ 14, $R_t$ 17, were finally selected for identification (peak A, 1-3 in FIG. 4). Prior to analysis, tetrabutylammonium was removed by solid phase extraction on $C_{18}$ silica.

Identification $R_t$ 8 was identified as imidazole-4-carboxaldehyde (ImCHO). Its UV-spectrum was identical to the synthesized (see below) reference compound with an absorption maximum of 257 nm. Co-injection of $R_t$ 8 with synthesized imidazole-4-carboxaldehyde resulted in a single chromatographic peak with a retention time of 8.13 minutes. Further evidence is to be collected (peak A in FIG. 4). The amount of ImCHO in the photooxidized UCA sample was gradually reduced upon storage at −20° C.

$R_t$ 10 was identified as imidazole-4-acetic acid. Its UV-spectrum was identical with an absorption maximum of 213 nm. Mass spectrum was obtained with electrospray technique and the dry sample was treated with methanol/HCl and n-butanol/HCl before analysis. A peak at mass 140 was obtained after methylation and at mass 183 after butylation. Consequently, the mass of the original compound was 126. Co-injection of $R_t$ 10 with commercially available imidazole-4-acetic acid resulted in a single chromatographic peak with a retention time of 8.98 minutes (peak 1 in FIG. 4).

$R_t$ 14 was identified as imidazole-4-carboxylic acid (ImCOOH). Its UV-spectrum was identical to the commercially obtained reference compound with an absorption maximum of 226 nm. Proton resonance (1H-NMR) analysis was done in $D_2O$, showing imidazolic protons in a ratio 1:1 with shifts of 7.76 and 7.53 ppm. Mass spectrum was obtained with electrospray technique and the dry sample was treated with methanol/HCl and n-butanol/HCl before analysis. A peak at mass 126 was obtained after methylation and at mass 169 after butylation. Consequently, the mass of the original compound was 112. Co-injection of $R_t$ 14 with commercially available ImCOOH resulted in a single chromatographic peak with a retention time of 14.73 minutes (peak 2 in FIG. 4). The amount of ImCOOH in the photooxidized UCA sample was gradually increased upon storage at −20° C.

Synthesis of imidazole-4-carboxaldehyde (4-formylimidazole; FW=134.5) from 4-(hydroxymethyl)imidazole-HCl.

538 mg starting material (4 mmol) was dissolved in ~4 ml methanol and 500 mg $NaHCO_3$ (6 mmol) was added. The tube was occasionally stirred for 60 min, alternatively at 4° C. and at warm water temperature. $CO_2$ was allowed to escape from the glass tube. The mix was divided across several Eppendorf tubes and subjected to Speedvac treatment for 1 hour. Residues were white solids with light-yellow sirupy liquids. Chloroform/methanol mix 1:1 was added to the tubes with subsequent gentle warming and stirring. $NaHCO_3$ was separated by centrifugation of the combined fractions at 3500 rpm for 5 min. Clear supernatant was kept overnight at −20° C. to allow the precipitation of additional $NaHCO_3$. Then, the solution was cleared by filtration and evaporated to dryness with a Rotavapor device. The residue was taken up in 20 ml dioxane with magnetic stirring and 4.4 mg $MnO_2$ (activated; for synthesis) was added in the same flask. The residue may not have been dissolved completely in first instantion. The mix was refluxed for 2 hours on a paraffin oil bath. The warm solution was filtered and $MnO_2$ was washed once with warm dioxane. Dioxane was evaporated with the Rotavapor® yielding a white and yellow fine cristalline solid. Crystallization was carried out in methanol repeated times. Small volumes of methanol were required, because the residue dissolved well in methanol.

| | |
|---|---|
| Yield: | ~20 mg (lit: ~475 mg) of fine off-white crystals. |
| M.p.: | 167-168° C. (lit: 173-175° C.) |
| M.p.: | 4-(hydroxymethyl)imidazole-HCl:108-111° C. |
| M.p.: | imidazole-4-carboxylic acid: 294-295° C. (lit.: Battersby AR et al., J Chem Soc (Perkin I) 43-51, 1980) |

The results show that similar sets of several UCA oxidation products can be formed with UV irradiation and without (Fenton reaction type). Three products were identified so far. We assume that these compounds occur in the upper layer of the epidermis as well and a method will be developed to determine UCA oxidation products in vivo. The simultaneous break-down of ImCHO and the gain of ImCOOH after photooxidation has led to our speculation that ImCHO is slowly oxidized to ImCOOH during storage. Many aldehydes are gradually oxidized to the corresponding carboxylic acids in contact with oxygen species.

Two phenomena out of the puzzling mechanism of cis-UCA induced immuno-suppression can be solved if UCA oxidation products would have immunosuppressive properties. First, the abrogation of the immunosuppression by antioxidants (19-21) in the model of contact hyper-sensitivity measuring ear swelling response. In our scope, the formation of UCA oxidation products is prevented, because of neutralization of the hydroxyl radicals by the antioxidants. Second, the lack of correlation between cis-UCA formation by UV-B and UV-A (18). No immunosuppression was found with UV-A irradiation, despite the fact that cis-UCA was formed. In our scope, this finding may be explained as the inability of UV-A to photooxidize UCA. Consequently, no UCA photooxidation products are formed with UV-A (results section) and because of that immunosuppression would not occur. Our findings and the above assumptions may point to a important role for UCA (photo)oxidation products in the skin immune system.

LEGENDS TO FIGURES

FIG. 1. Compounds tested in this study for hydroxyl radical scavenging ability. (a) trans-UCA, (b) cis-UCA, (c) L-histidine, (d) dihydroUCA or 3-(imidazol-4-yl)propionic acid, (e) imidazole acetic acid, (f) 2-methylimidazole, (g) imidazole, (h) L-alanine, (i) trans-2-furylacrylic acid and (j) uric acid.

FIG. 2. A determination of the second order rate constants of trans-UCA and cis-UCA with hydroxyl radicals. The rate constant was derived from the slope of the line ($k=slope \times k_{dR} \times [dR] \times A_0$), where $A_0$ is the absorbance, measured in the absence of hydroxyl radical scavenger. $K_{dR}$ was taken as $3.1 \times 10^9$ $M^{-1} \cdot s^{-1}$, derived from pulse radiolysis studies [8], and [dR]=3 mM. The rate constants in this particular set were 8.49 and $7.33 \times 10^9$ $M^{-1} \cdot s^{-1}$ for trans-UCA and cis-UCA, respectively. The other scavengers were studied similarly.

FIGS. 3A-3D. Chromatograms of 80 µM trans-urocanic acid in 20 mM phoshate buffer pH 7.2. The initial concentration of hydrogen peroxide was 500 µM. Injection volume was 80 µL.

a. with hydrogen peroxide; not irradiated, b. without hydrogen peroxide; irradiated with a WG280 filtered xenon-arc lamp, c. with hydrogen peroxide and irradiated as 1b, d. with hydrogen peroxide and irradiated with a WG335 filtered xenon-arc lamp. Peaks assigned with A-H correspond with photooxidation products. Separation was performed on a Alltima $C_{18}$ column with UV detection at 210 nm. The eluent consisted of 10 mM sodium phosphate pH 7.2 with 1.0 mM tetrabutylammonium hydrogen sulphate. Further experimental conditions are described in the text.

FIG. 4. Comparable chromatographic patterns in the formation of UCA oxidation products from 80 µM trans-UCA and 500 µM hydrogen peroxide in water (no buffer). Left: after Fenton oxidation with 250 µM $Fe^{2+}$ and right:. after photooxidation with 'full' UV, containing a UV-B dose of 32 $kJ \cdot m^{-2}$. The cis-UCA peak is missing after Fenton oxidation, due to the absence of photoisomerization. Peak assignation (A-G) was done as in FIG. 1c. Peaks B,C and D refer to imidazole-4-carboxaldehyde, imidazole-4-acetic acid and imidazole-4-carboxylic acid, respectively. Chromatographic conditions were identical to those applied in FIG. 3.

FIG. 5. Inhibition of contact hypersensitivity as a reduction of ear swelling response from BALB/c mice. The positive control (no inhibition) was normalized to 100%. Im-mix is a mix of the three identified imidazoles (see, identifications) and POmix III is a mix of the three identified imidazoles among several other unidentified UCA oxidation products, obtained upon extensive photooxidation. Rudimental trans- and cis-UCA are present in lower amounts than 3% (by weight).

REFERENCES

1. Morrison, H. (1985) Photochemistry and photobiology of urocanic acid. Photodermatology 2, 158-165.
2. Gibbs, N. K., M. Norval, N. J. Traynor, M. Wolf, B. E. Johnson and J. Crosby (1993) Action spectra for the trans to cis photoisomerisation of UCA in vitro and in mouse skin. Photochem. Photobiol. 57, 584-590. Correction (1993) Photochem Photobiol 58, 769.
3. Kammeyer, A., M. B. M. Teunissen, S. Pavel, M. A. de Rie M A and J. D. Bos (1995) Photoisomerization spectrum of urocanic acid in human skin and in vitro: effects of simulated solar and artificial UV-radiation. Br. J. Dermatol. 132, 884-891.
4. Anglin Jr J H (1976) Urocanic acid, a natural sunscreen. Cosmet Toiletries 91, 47-49.
5. Norval M., N. K. Gibbs and J. Gilmour (1995) The role of urocanic acid in UV-induced immunosuppression: recent advances (1992-1994). Photochem. Photobiol. 62, 209-217, 1995.
6. Darr D. and I. Fridovich (1994) Free radicals in cutaneous biology. J. Invest. Dermatol. 102, 671-675.
7. Black H. (1987) Potential involvement of free radical reactions in ultraviolet-light mediated cutaneous damage. Photochem. Photobiol. 46, 213-221
8. Noonan F. P. and E. C. De Fabo (1992) Immunosuppression by UV-B radiation: initiation by urocanic acid. Immunology Today 13, 250-254.
9. Ross J. A., S. E. M. Howie, M. Norval and J. Maingay (1988), Systemic administration of urocanic acid generates suppression of the delayed type of hypersensitivity response to Herpes simplex virus in a murine model of infection, Photodermatology 5, 9-14.

10. Gruner S., W. Diezel, H. Stoppe, H. Oesterwitz and W. Henke (1991) Inhibition of skin allograft rejection and acute graft versus-host disease by urocanic acid. J. Invest. Dermatol. 98, 459-462.
11. De Fabo E. C., F. Noonan, M. Fischer, J. Burns and H. Kacser (1983) Further evidence that the photoreceptor mediating UV-induced systemic immune suppression is urocanic acid. J. Invest. Dermatol. 80, 319.
12. Reilly S. K. and E. C. De Fabo (1991), Dietary histidine increases mouse skin urocanic acid levels and enhances UV-B induced immunosuppression of contact hypersensitivity, Photochem Photobiol 53, 431-438.
13. Beissert S., T. Mohammad, H. Torri, A. Lonati, Z. Yan, H. Morrison and R. D. Granstein (1997), Regulation of tumor antigen presentation by urocanic acid, J. Immunol. 159, 92-96.
14. Redondo P., J. Garcia-Foncillas, F. Cuevillas, A. Espana and E. Quintanilla (1996). Effects f low concentrations of cis- and trans-urocanic acid on cytokine elaboration by keratinocytes, Photodermatol Photoimmunol Photomed 12, 237-243.
15. Lappin M. B., J. M. Weiss, E. Schopf, M. Norval and J. C. Simon (1997), Physiologic doses of urocanic acid do not alter the allostimulatory function or the development of murine dendritic cells in vitro, Photodermatol Photoimmunol Photomed 13, 163-168.
16. Higaki Y., C. Hauser, G. Siegenthaler and J H Saurat (1986) Cis-urocanic acid does not inhibit mitogen induced lymphocyte transformation in man. Acta Derm. Venereol. (Stockh) 66, 523-526.
17. Rattis F. M., J. Péguet-Navarro, P. Courtellemont, G. Redziniac and D. Schmitt (1995) Cis-urocanic acid failed to affect in vitro human Langerhans cell allostimulatory function. Photochem. Photobiol 62, 914-916.
18. Reeve V., C. Boehm-Wilcox, M. Bosnic, R. Cope and R. D. Ley (1994) Lack of correlation between suppression of contact hypersensitivity by UV radiation and photo-isomerization of epidermal urocanic acid in the hairless mouse. Photochem. Photobiol. 60, 268-273.
19. Reeve V. E., M. Bosnic and E. Rozinova (1993) Carnosine protects from suppression of contact hypersensitivity by UV-B radiation or by cis-urocanic acid. Immunology 78, 99-104.
20. Reeve V. E., M. Bosnic, E. Rozinova and C. Boehm-Wilcox (1993) A garlic extract protects from UV-B radiation induced suppression of contact hypersensitivity. Photochem. Photobiol. 58, 813-817.
21. Hemelaar P. J. and G. M. J. Beijersbergen van Henegouwen (1996) The protective effect of N-acetylcysteine on UV-B induced immunosuppression by inhibition of the action of cis-urocanic acid. Photochem. Photobiol. 63, 322-327.
22. Halliwell B., J. M. C. Gutteridge and O. I. Aruoma (1987) The deoxyribose method: a simple "test tube" assay for the determination of rate constants for reactions of hydroxyl radicals. Anal. Biochem. 165, 215-219.
23. Lewisch S. A. and R. L. Levine (1995) Determination of 2-oxohistidine by amino acid analysis. Anal. Biochem. 231, 440-446.
24. Aruoma O. I., M. J. Laughton and B. Halliwel (1989) Carnosine, homocarnosine and anserine: could they act as antioxidants in vivo ? Biochem. J. 264, 863-869.
25. Zhao M J and Jung L (1995) Kinetics of the competitive degradation of deoxyribose and other molecules by hydroxyl radicals produced by the Fenton reaction in the presence of ascorbic acid. Free Radical Res 23, 229-243.
26. Gorodetsky R., J. Sheskin, A. Weinreb (1986) Iron, copper and zinc concentrations in normal skin and in various nonmalignant and malignant lesions. Int. J. Dermatol. 25, 440-445.
27. Goldblum W. R., S. Derby and A. B. Lerner (1953) The metal content of skin, nails and hair. J. Invest. Dermatol. 20, 13-18.
28. Aubailly M., R. Santus and S. Salmon (1991) Ferrous ion release from ferritin by UV-A radiations. Photochem. Photobiol. 54, 769-773.
29. Boveris A., N. Oshino and B. Chance (1972) The cellular production of hydrogen peroxide. Biochem. J. 128, 617-630.
30. Mc Cormick J. P., J. R. Fischer and J. P. Patchlatko (1976) Characterization of a cell lethal product from the photo-oxidation of tryptophan: hydrogen peroxide. Science 191, 468-469.
31. Hu M. L. and A. L. Tappel (1992) Potentiation of oxidative damage to proteins by UV-A and protection by antioxidants. Photochem. Photobiol. 56, 357-363.
32. Jurkiewicz B. A., D. L. Bisset and G. R. Buettner G R (1993) Effect of topically applied tocopherol on UV-radiation-mediated free radical damage in skin. J. Invest. Dermatol. 104, 484-488.
33. Ching T. L., R. M. Vanderhee, N. M. Bhoelan, J. Blauw, W. M. P. B. Menge, J. De Jong and A. Bast (1995) Histamine as a marker for hydroxyl radicals. Mediators of Inflammation 4, 339-343.
34. Babizhayev M. A., M. C. Seguin, J. Gueyne, R. P. Evstigneeva, E. A. Ageyeva and G. A. Zheltukhina (1994) L-Carnosine and carcinine act as natural antioxidants with hydroxyl-radical-scavenging and lipid-peroxidase activities. Biochem. J. 304, 509-516.
35. Ching T. L., G. R. M. M. Haenen and A. Bast (1993) Cimetidine and other $H_2$ receptor antagonists as powerful hydroxyl radical scavengers. Chem. Biol. Interactions 86, 119-127.

TABLE 1

THE HYDROXYL RADICAL SCAVENGING ABILITY OF UROCANIC ACID ISOMERS AND RELATED COMPOUNDS.

| HYDROXYL RADICAL SCAVENGER | SECOND ORDER RATE CONSTANT × $10^9$ $M^{-1} \cdot s^{-1}$ S.D. $n^{(b)}$ | | INHIBITION of DEOXYRIBOSE DEGRADATION [SCAVENGER] = [DEOXYRIBOSE] = 3 Mm % |
|---|---|---|---|
| IMIDAZOLES | | | |
| trans-Urocanic acid | 8.0 | 0.9 8 | 67 |
| cis-Urocanic acid | 7.1 | 0.6 6 | 64 |
| L-Histidine | 2.6[c] | 0.9 4 | 34 |
| Dihydrourocanic acid | 2.7 | 0.9 3 | 34 |
| Imidazole-4acetic acid | 2.2 | 0.1 3 | 30 |
| 2-Methylimidazole | 11.7 | 2.6 5 | 76 |
| OTHER COMPROUNDS | | | |
| L-Alanine | 0.1 | 0.0 3 | 2 |
| trans-2-Furylacylic acid[a] | < 0.1 | — 3 | <2 |
| Uric acid | 27.8 | 3.0 4 | 91 |

[a] trans-2-furylacrylic acid was not tested in concentrations >8 mM because of poor solubility.
[b] n represents the number of slopes from which the rate was calculated.
[c] 2.3-3.0 × $10^9$ $M^{-1} \cdot s^{-1}$ in literature [22]

TABLE 2

UROCANIC ACID (UCA) ISOMERS[1] after PHOTOOXIDATION

| UV RADIATION SOURCE | SPECTRAL CHARACTER-ISTICS | | DOSE kJ·m$^{-2}$ UV-B UV-A | UCA LEFT OVER % (±SD)[2] | YIELD OF PHOTO-OXIDATION PRODUCTS A.U.[3] (±S.D.)[2] | PHOTOISO-MERIZATION[4] trans-UCA % (±SD)[2] | cis-UCA % |
|---|---|---|---|---|---|---|---|
| Xe arc | WG280 UV-C, -B, -A included | 270-400 nm | 37 70 | 43 (±11) | 347 (±58) | 41 (±2) | 59 |
| Xe arc | WG305 UV-B, -A included | 292-400 nm | 18 70 | 64 (±6) | 219 (±14) | 47 (±3) | 53 |
| Xe arc | WG335 only UV-A included | 320-400 nm | 0 66 | 96 (±5) | 45 (±8) | 60 (±2) | 40 |
| TL12[5] | unfiltered | 280-366 nm | 3.6 4.5 | 90 (±20) | 149 (±51) | 41 (±4) | 59 |
| TL10R[5] | unfiltered | 320-440 nm | 0 324 | 99 (±3) | 16 (±5) | 84 (±7) | 16 |

[1]Initial concentration of trans-UCA or cis-UCA is 40 µM and that of hydrogen peroxide 500 µM
[2]Standard Deviation (S.D.) of duplicate measurements.
[3]A.U.: Arbitrary Units derived from peak area integration. The peaks of 8 major products were summed.
[4]This listing only applies to trans-urocanic acid as starting material.
[5]Philips' fluorescent tubes. Different spectral distribution and radiometric measurements as compared to xenon-arc.

TABLE 3

TRANS-UROCANIC ACID[1] after FENTON OXIDATION

| [Fe$^{2+}$][2] (µM) | TRANS-UROCANIC ACID LEFT OVER % (±S.D.)[5] | | YIELD of FENTON OXIDATION PRODUCTS A.U.[4] (±S.D.)[5] | |
|---|---|---|---|---|
| | in phosphate buffer[3] | in water | in phosphate buffer[3] | in water |
| 0   | 100 (±1)  | 100 (±3) | <10     | <10 |
| 50  | 97 (±1)   | 77 (±11) | <10     | 194 (±34) |
| 100 | 94 (±6)   | 48 (±7)  | 27 (±5) | 272 (±6) |
| 250 | 83 (±3)   | 19 (±8)  | 36 (±3) | 423 (±76) |
| 500 | 78 (±12)  | <4       | 49 (±9) | 511 (±35) |

[1]Initial trans-UCA concentration: 40 µM.
[2]Fe$^{2+}$ added before hydrogen peroxide.
[3]10 mM sodium phosphate buffer, pH 7.2
[4]A.U.: Arbitrary Units derived from peak area integration. The peaks of 8 major products were summed.
[5]Standard Deviation (S.D.) of duplicate measurements.

The invention claimed is:

1. A pharmaceutical composition comprising urocanic acid or functional equivalent thereof, and imidazole-4-carboxaldehyde, imidazole-4-carboxylic acid or a combination thereof.

2. A pharmaceutical composition comprising at least two of imidazole-4-carboxaldehyde, imidazole-4-carboxylic acid, imidazole-4-acetic acid, 3-(4-imidazolon-2yl)-acrylic acid or 3-(4-imidazolon-5-yl)-acrylic acid.

3. A pharmaceutical composition comprising urocanic acid or a functional equivalent thereof, and at least one of imidazole-4-carboxaldehyde, imidazole-4-carboxylic acid, imidazole-4-acetic acid, 3-(4-imidazolon-2-yl)-acrylic acid or 3-(4-imidazolon-5-yl)-acrylic acid.

4. A pharmaceutical composition according to claim 1, wherein the urocanic acid is trans-urocanic acid.

5. A pharmaceutical composition according to claim 3, wherein the urocanic acid is trans-urocanic acid.

6. A pharmaceutical composition according to claim 1, wherein the urocanic acid is cis-urocanic acid.

7. A pharmaceutical composition according to claim 3, wherein the urocanic acid is cis-urocanic acid.

* * * * *